United States Patent
Stalnaker et al.

(10) Patent No.: US 6,439,041 B1
(45) Date of Patent: Aug. 27, 2002

(54) POWDER DISPENSING/COLLECTION MANIFOLD FOR INDOOR WEAR TESTING

(75) Inventors: David O. Stalnaker, Hartville; Richard J. Macioce, Massillon; Craig McClung, Massillon; Daniel Hentosz, Sr., Akron, all of OH (US)

(73) Assignee: Bridgestone/Firestone North American Tire, LLC, Nashville, TN (US)

( * ) Notice: Subject to any disclaimer, the term of this patent is extended or adjusted under 35 U.S.C. 154(b) by 0 days.

(21) Appl. No.: 09/634,570

(22) Filed: Aug. 9, 2000

(51) Int. Cl.[7] ............................................. B60C 23/02
(52) U.S. Cl. ....................................................... 73/146
(58) Field of Search ........................... 73/146, 148, 431, 73/7, 8, 9; 15/302; 222/92; 340/442

(56) References Cited

U.S. PATENT DOCUMENTS

| | | | |
|---|---|---|---|
| 3,899,917 A | | 8/1975 | Kisbany |
| 5,237,801 A | * | 8/1993 | Hillam et al. .................. 53/446 |
| 5,504,968 A | * | 4/1996 | Pressley ....................... 15/302 |
| 5,634,236 A | | 6/1997 | Darsey |
| 5,703,284 A | | 12/1997 | Gerhards et al. |
| 5,783,044 A | | 7/1998 | Schneider et al. |
| 5,964,956 A | | 10/1999 | Straub et al. |
| 6,161,724 A | * | 12/2000 | Blacker et al. ................ 222/23 |

* cited by examiner

Primary Examiner—Benjamin R. Fuller
Assistant Examiner—Jewel V. Thompson
(74) Attorney, Agent, or Firm—Meredith Palmer; Michael Sand

(57) ABSTRACT

A powder dispensing/collection device for indoor testing of pneumatic tires includes a first outer housing (12) having an open end (24) facing a road wheel (94). First and second adjustable shrouds (28), (32) are disposed on an upper and lower portion of the outer housing respectfully. The shrouds are selectively moveable in a direction perpendicular to a width (w) of the outer housing. A second inner housing (48) is partially enclosed by the outer housing and has an open end (64) facing the road wheel which protrudes out from the outer housing a predetermined distance. At least one of the outer walls of the inner housing and the inner walls of the outer housing define a vacuum collection chamber (76). The inner housing is manually moveable within the outer housing so that the distance between the open end of the inner housing and the road wheel can be adjusted. A hose (78) extends through an aperture (80) in the inner housing and into the dispensing chamber. A spray nozzle (84) is connected to the free end of the hose. The position of the spray nozzle within the dispensing chamber is adjustable by manually moving the nozzle backward or forward within the inner housing. At least one vacuum duct (82a, 82b) is operatively connected to a rear wall (22) of the outer housing for transferring a vacuum force to the vacuum collection chamber.

19 Claims, 4 Drawing Sheets

POWDER DISPENSING/COLLECTION MANIFOLD FOR INDOOR WEAR TESTING

FIELD OF THE INVENTION

Figure 1:
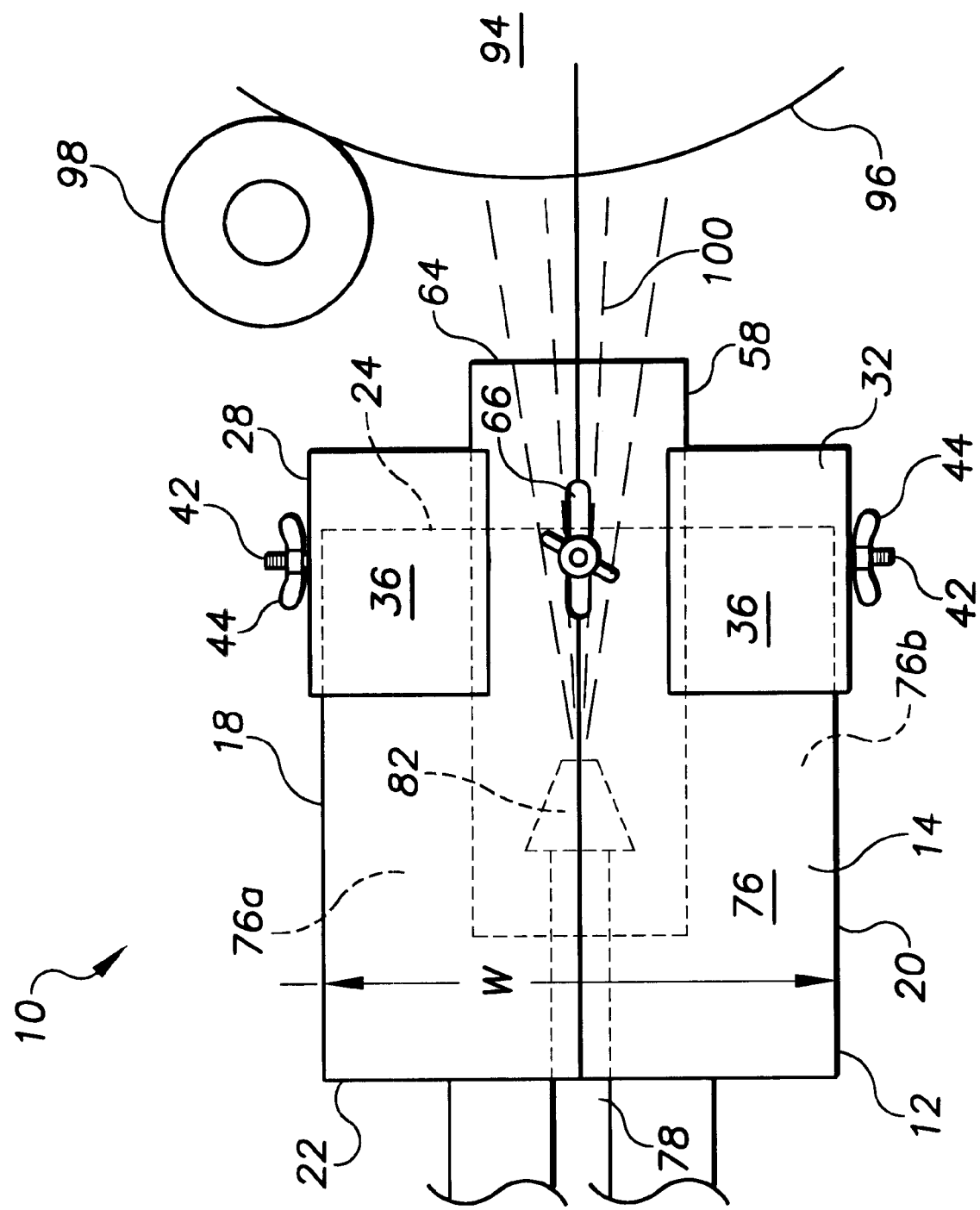

The present invention pertains generally to the art of pneumatic tire testing systems adapted for indoor use. More particularly, the present invention relates to a new and improved device for dispersing a powder substance onto a wear surface during indoor tirewear testing in order to prevent particle build-up or gumming on the outer surface of the tire and wear surface.

Discussion of the Prior Art

A conventional pneumatic tire for cars, trucks, etc. is generally fabricated from elastomeric materials, such as cured rubber products. After the pneumatic tire is mounted on a vehicle, it typically undergoes compressive, tensile and shearing forces as it travels along a road surface. Such forces will inevitably cause particles to be worn from the tire tread and oils to be released from the rubber material. Over an extended period of time, the tire will wear to a point that it will have to be replaced.

Tire manufacturers often test their tires in order to determine how the tires will perform under typical and/or extreme driving conditions. In addition, tire testing is helpful for detecting manufacturing problems. The information resulting from tire testing is important for learning how tires can be improved in terms of safety, length of life, and performance. However, it is difficult to conduct reliable tire testing unless the tires are actually put on a vehicle and driven on a variety of surfaces for an extended period of time. Such testing is obviously not practical. Thus, manufacturers have developed indoor or laboratory tire testing systems which attempt to recreate and expose tires to actual driving conditions.

Laboratory tire wear testing is a relatively new field of technology. In a typical indoor testing process, a tire is loaded against a rotating road wheel which has an abrasive surface attached thereto. The tire and rotating road wheel are designed to simulate actual driving conditions. As the road wheel rotates against the tire, tire particles and oils are released and tread rubber is slowly worn away.

Under actual driving conditions a vehicle moves relative to the road surface. Thus, the released particles are immediately dispersed away from the tire and, therefore, have negligible influence on the tire performance. In contrast, during indoor tire testing, the tire is loaded against the road wheel and rotated at a fixed reference point. As a result, the worn particles circulate and accumulate around the surfaces of the tire and abrasive surface. The particles have oils which cause them to become soft and sticky. Thus, the released materials adhere to the tire tread and/or abrasive surface, masking the performance of the tire tread and hindering the acquisition of accurate data.

One known solution for preventing the abraded gummy rubber particles from adhering to the tire and/or abrasive surface is to introduce a powder substance onto the abrasive surface of the rotating road wheel as the tire is being tested. Any variety of powders may be used, such as fluidized talcum powder. The powder, when dusted or sprayed onto the wear surface, will adhere to or absorb the released particles and minimize the occurrence of abrading and gumming.

Fluidized powder spray equipment designed specifically for minimizing gumming and abrading is known and commercially available. However, known powder spraying devices suffer from a number of shortcomings. First, they are unable to achieve a consistent and controlled application of the powder to the abrasive surface. Second, they do not collect excess powder before it is caught in the turbulent air stream of the rotating wheel and dispersed throughout a large working environment. Third, they are not capable of conducting wear testing in both directions of rotation. Finally, they do not allow for the powder dispensing nozzle to be disposed at different positions relative to the road wheel.

Accordingly, a need exists to provide a powder dispensing/collecting device for indoor tire testing applications which overcomes the foregoing problems and others.

SUMMARY OF THE INVENTION

In accordance with one aspect of the present invention, a powder dispensing and collection device for testing of pneumatic tires includes a first housing having an open end facing an abrasive surface of an associated road wheel. A second housing, which is at least partially enclosed by the first housing, defines a dispensing chamber. The second housing has an open end facing the abrasive surface of the road wheel. At least one interior surface of the first housing and at least one exterior surface of the second housing define a vacuum collection chamber. A dispensing mechanism is operatively connected to the second housing and is located within the dispensing chamber. The dispensing mechanism is configured to apply a media to the abrasive surface.

In accordance with another aspect of the present invention, a testing device for pneumatic tires includes a road wheel having an outer abrasive surface. A first housing encloses a vacuum collection chamber. The first housing has an open end adjacent the abrasive surface of the road wheel. A second housing is disposed adjacent the abrasive surface of the road wheel and defines a dispensing chamber. The second housing has an open end facing the abrasive surface. A dispensing mechanism is operatively connected to the second housing and is located within the dispensing chamber. The dispensing mechanism is configured to apply an absorbent media to the abrasive surface of the road wheel.

In accordance with another aspect of the present invention, a method for dispersing and collecting an absorbent media during testing of a pneumatic tire includes loading a tire against an abrasive surface of a road wheel and positioning an inner housing adjacent the abrasive surface of the road wheel and within an outer housing. Apply a media to the abrasive surface of the road wheel via a spray nozzle which is disposed within a dispensing chamber defined by the inner housing. Excess absorbent media and worn particles which fall from the abrasive surface and surrounding area are vacuumed into a vacuum collection chamber which is enclosed by the second housing. The excess absorbent media and worn particles are transferred from the vacuum collection chamber to at least one vacuum duct communicating with the vacuum collection chamber.

One advantage of the present invention is the provision of a dispensing/collection device for indoor testing of pneumatic tires which minimizes the occurrence of particle build-up and gumming.

Another advantage of the present invention is the provision of a dispensing/collection device for indoor testing of pneumatic tires which vacuums and removes excess powder during testing which would otherwise be dispersed throughout a large working environment.

Another advantage of the present invention is the provision of a dispensing/collection device for indoor testing of pneumatic tires having a stagnant air column through which a powder stream travels before being applied to a road wheel, thereby allowing for a more consistent and controlled application of the powder to an abrasive surface of the road wheel.

Figure 4:
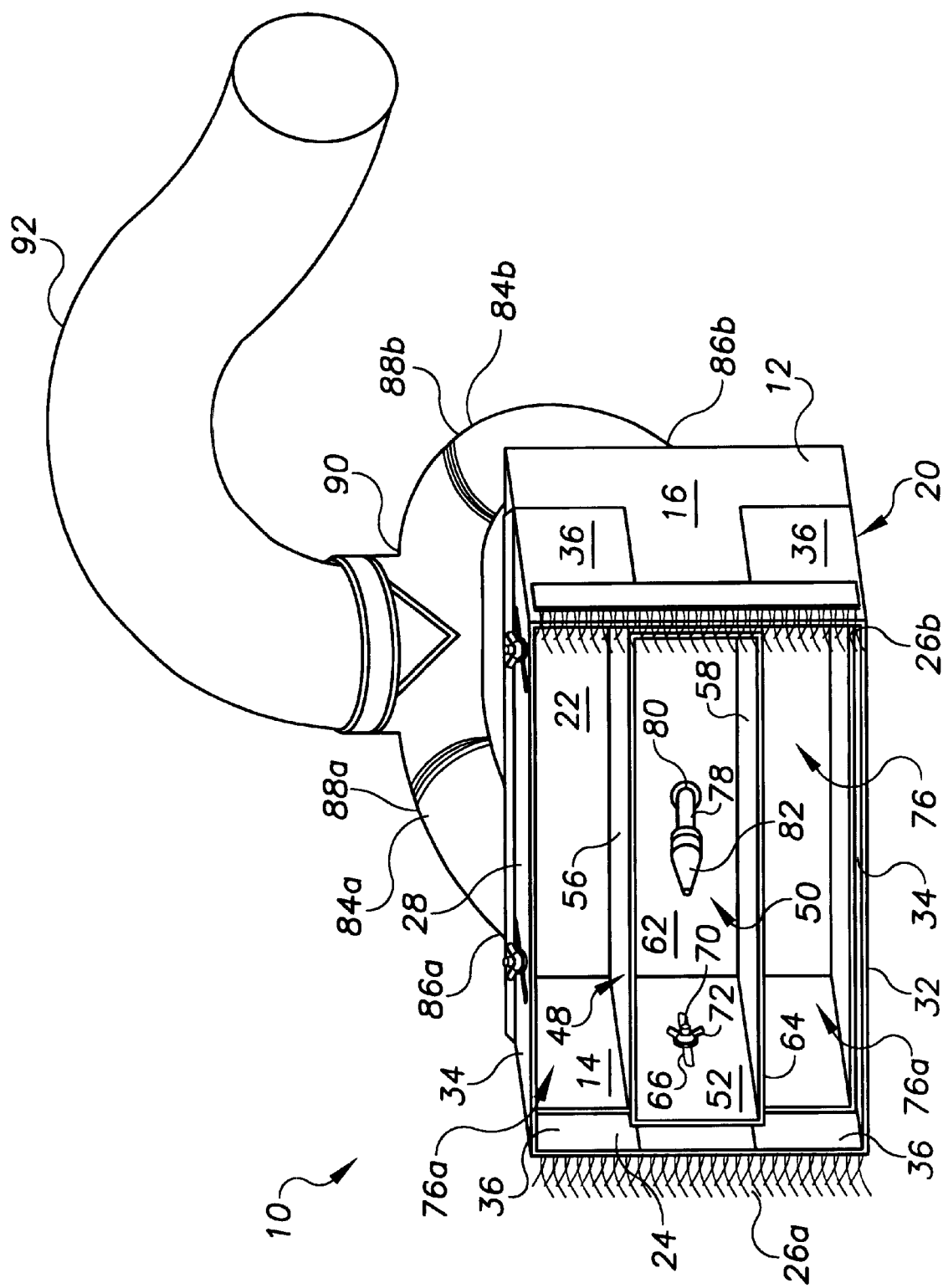

Another advantage of the present invention is the provision of a dispensing/collection device for indoor testing of pneumatic tires having adjustable shrouds which enable an operator to regulate the position of a vacuum collection chamber relative to a road wheel and the suction force of the device.

Yet another advantage of the present invention is the provision of a dispensing/collection device for indoor testing of pneumatic tires having a nozzle that can effectively apply a powder to a testing surface at a distance relatively far away from the testing surface.

Still another advantage of the present invention is the provision of a dispensing/collection device for indoor testing of pneumatic tires that is capable of effectively conducting wear testing in either direction of rotation.

Still other benefits and advantages of the invention will become apparent to those skilled in the art upon reading and understanding the following detailed specification.

BRIEF DESCRIPTION OF THE DRAWINGS

The invention may take physical form in certain parts and arrangements of parts, several embodiments of which will be described in detail in this specification and illustrated in the accompanying drawings which form a part hereof and wherein:

FIG. 1 is a top plan view of a dispensing/collection device in accordance with the present invention;

FIG. 2 is a side view of a dispensing/collection device in accordance with the present invention;

FIG. 3 is a perspective view of a dispensing/collection device in accordance with the present invention; and FIG. 4 is a front perspective view of a dispensing/collection device in accordance with the present invention.

DETAILED DESCRIPTION OF A PREFERRED EMBODIMENT

Reference will now be made in detail to the present preferred embodiment of the invention, an example of which is illustrated in the accompanying drawings. While the invention will be described in connection with the preferred embodiment, it will be understood that it is not intended to limit the invention to that embodiment. On the contrary, it is intended to cover all alternatives, modifications and equivalents that may be included within the spirit and scope of the invention defined by the appended claims.

With reference to FIGS. 1–3, a powder dispensing/collection device 10 for applying a powder substance to a wear surface during laboratory testing of pneumatic tires is shown in accordance with the present invention. The dispensing/collection device includes a first outer housing 12 defined by opposing sidewalls 14, 16, an upper and lower wall 18, 20, and a rear wall 22. An open end 24 of the outer housing 12 provides access into its interior. Brush members 26*a*, 26*b* are operatively connected to opposing side portions of the dispensing/collection device adjacent open end 24. The outer housing is preferably constructed from a rigid material, such as galvanized steel. However, other materials are contemplated by the present invention.

First and second adjustable shrouds 28, 32 are disposed on an upper and lower portion of the outer housing respectively. Each shroud includes a substantially rectangular planar section 34 extending across a width w of the outer housing and a side section 36 extending perpendicularly from each edge of section 34. The shrouds are selectively moveable in a direction perpendicular to the width w of the outer housing. More particularly, a pair of slits 40*a*, 40*b* are provided in the planar section 34 of each shroud. Threaded bolts 42, which are tightened and loosened with wing nuts 44, extend through the upper and lower walls 18, 20 of housing 12 and through the slits of each shroud. When the wing nuts are loosened, the shrouds are free to slide forward and backward a distance equal to the length of the slits.

With continued reference to FIG. 3 and further reference to FIG. 4, the dispensing/collection device 10 includes a second inner housing 48 partially enclosed by housing 12 which defines a dispensing chamber 50. Like housing 12, housing 48 includes opposing sidewalls 52, 54, an upper and lower wall 56, 58, and a rear wall 62. In order to secure the inner housing within the outer housing, the sidewalls of housing 48 are fastened to the sidewalls of housing 12 using conventional fasteners or fastening means. The inner housing has a height which is less than the height of the outer housing and a width which is substantially equal to the width of the outer housing.

An open end 64 of the inner housing provides egress from the dispensing chamber 50. The open end of housing 48 protrudes a predetermined distance out of housing 12. The length that housing 48 extends out from housing 12 is preferably adjustable. To adjust this length, at least one slit 66 is disposed on each sidewall 52, 54 of the inner housing. A threaded bolt 70, which is tightened and loosened with a wing nut 72, extends through each sidewall 14, 16 of housing 12 and into slit 66. When the wing nuts are loosened, housing 48 is free to slide forward and backward a distance equal to the length of slit 66. Alternatively, flanges (not shown) extend inwardly from the walls of the outer housing and provide support brackets which the inner housing may rest on. To adjust the position of the inner housing, it is simply slid along the support brackets.

The interior surfaces of the outer housing's walls and the exterior surfaces of the upper and lower walls 56, 58 and rear wall 62 of the inner housing define a substantially "C" shaped vacuum collection chamber 76 (see FIG. 1). The vacuum collection chamber includes a top cavity 76*a* and a bottom cavity 76*b* which facilitates testing in either direction of tire rotation. A hose or conduit 78 (see also FIGS. 1 and 2) extends through the outer housing 12, through the vacuum collection chamber, through an aperture 80 in the inner housing 48 and into the dispensing chamber 50. The conduit is connected to a spray nozzle 82 located in the dispensing chamber. The position of the spray nozzle within the dispensing chamber is adjustable by manually moving the spray nozzle backward or forward within the inner housing. Since the aperture 80 in the inner housing is manufactured with a clearance, conduit 78 is free to slide back and forth therein. Once the spray nozzle is placed in a desired position, a conventional fastening means (not shown) is provided on the rear wall 62 of the inner housing to secure the nozzle in place.

With continued reference to FIGS. 3 and 4, the powder dispensing/collection device 10 further includes first and second vacuum ducts 84*a*, 84*b* each having a first end 86*a*, 86*b* and a second end 88*a*, 88*b*. The first end of ducts 84*a* and 84*b* are operatively connected to the rear wall 22 of the outer housing 12 and are disposed in a horizontal plane substantially the same as that in which the inner housing is disposed. Thus, the first and second ducts are hidden behind the inner housing and, therefore, can not be seen in FIG. 4. The second end of ducts 84*a* and 84*b* are attached to a manifold 90. A main vacuum conduit 92 extends from the manifold and is connected to a vacuum source (not shown). The vacuum source provides a sucking force or vacuum force to the vacuum collection chamber 76 via the first and second ducts 84*a*, 84*b*.

Figure 2:
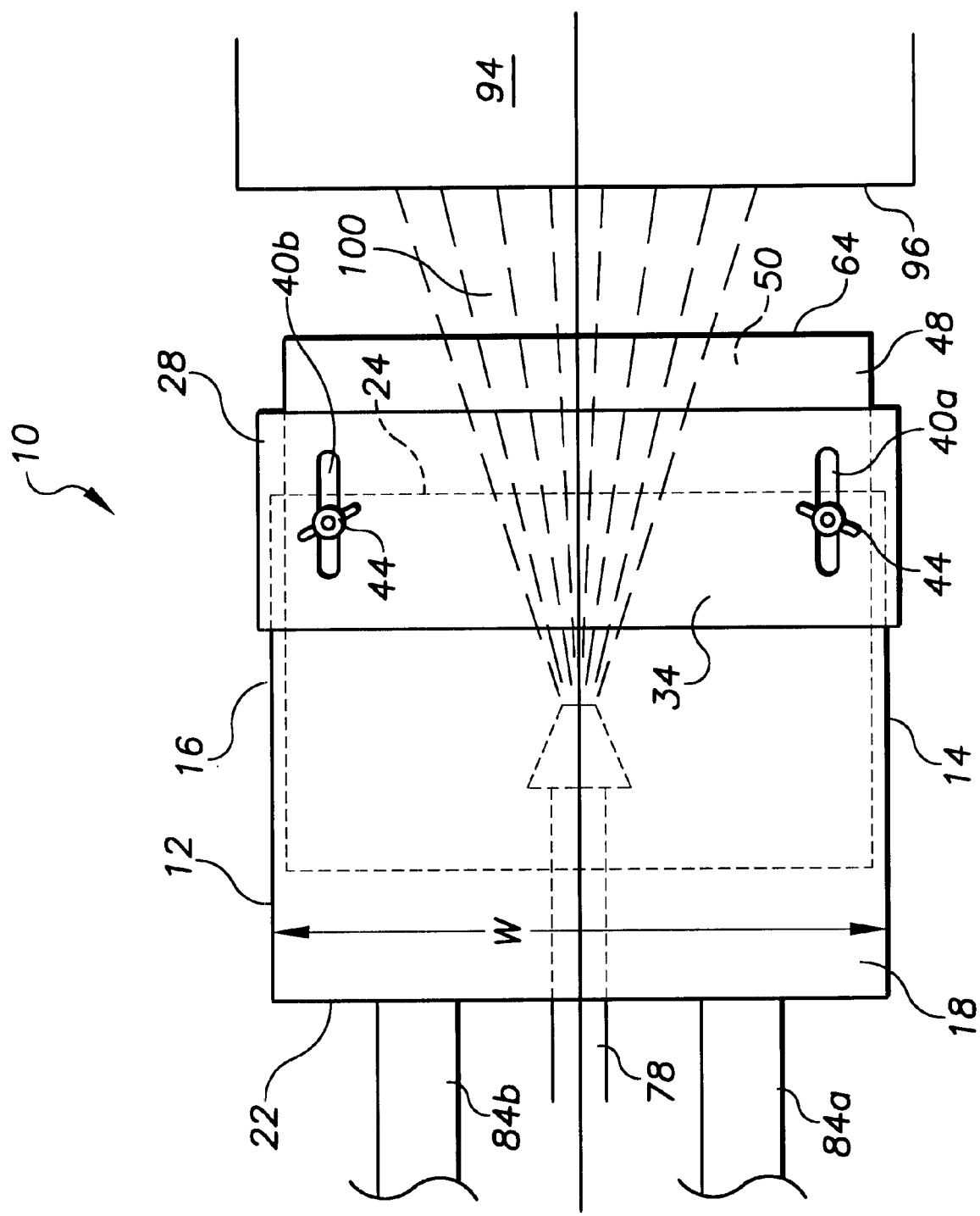
Figure 3:
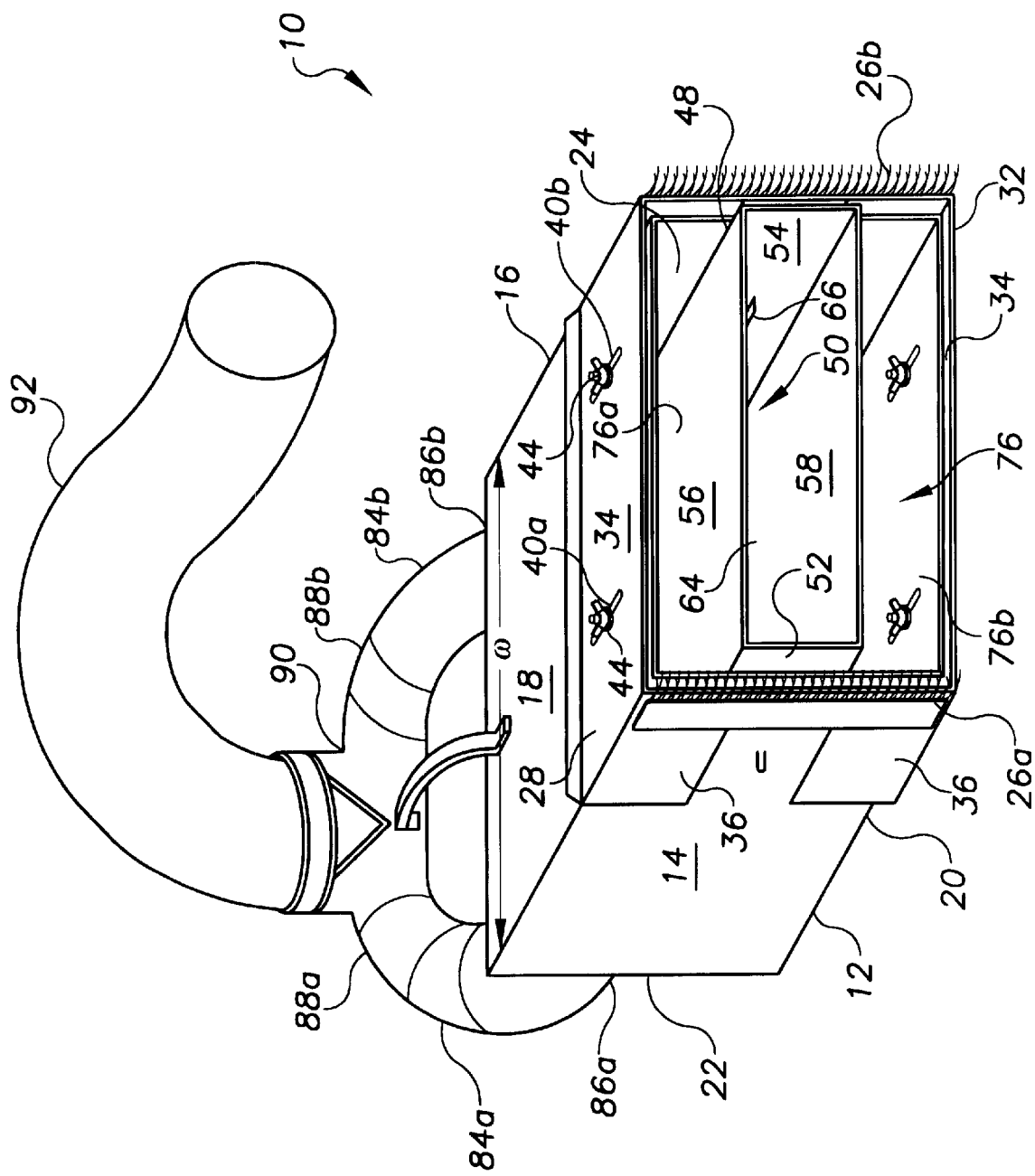

In operation, the powder/dispensing device is positioned so that the open end 24 of the outer housing 12 and the open end 64 of the inner housing 48 are located adjacent a road wheel 94 (see FIGS. 1 and 2) having an abrasive surface 96. A pneumatic tire 98 is loaded against the abrasive surface of the road wheel. The road wheel is rotated causing the pneumatic tire to rotate therewith. As the tire rotates, a plurality of tread particles are worn from the tire tread and oils are secreted from the rubber. The oils and released material combine to form sticky particles which have a tendency to adhere to the tire being tested as well as the abrasive surface of the road wheel. This masks the performance of the tire and hinders the acquisition of reliable testing data.

In order to prevent sticking and gumming, an absorbent or desiccant substance 100, such as fluidized talcum powder, is provided from conduit 78 to nozzle 82. The nozzle sprays the fluidized talcum powder onto the abrasive surface 96 of the road wheel 94. The powder operates as a drying agent on the released particles. As a result, the particles lose their stickiness and fall from the road wheel and tire rather than stick thereto and cause gumming problems. As the particles and excess powder fall from the abrasive surface of the road wheel and tire, the vacuum force in the vacuum collection chamber 76 sucks them into the inner housing and out through the first and second vacuum ducts 84*a*, 84*b*. This eliminates having to manually clean excess powder and tread particles that would otherwise be spread throughout a large working area.

There are several other advantages to the design of the present dispensing/collection device. First, the inner housing 48 is capable of moving backward and forward within the outer housing 12. Thus, the inner housing can be moved to a position immediately adjacent the abrasive surface 96 of the road wheel 94 (preferably within ½ of an inch). Such a placement provides a stagnant air column that improves the delivery of the air stream containing the fluidized powder. More specifically, the walls of the inner housing block the turbulent air currents produced by the rotation of the road wheel and the tire, thereby protecting the fluidized stream of powder exiting nozzle 82. This allows for a more consistent and controlled application of the powder to the abrasive surface of the road wheel.

A second advantage is gained due to the fact that the first and second shrouds 28, 32 are moveable in the forward and rearward directions. By extending the adjustable shrouds forward to a position closer to the road wheel 94, a stagnant air path is provided which enhances the suction force within the vacuum collection chamber 76. An enhanced suction force is achieved because the walls of the shrouds will protect the suction force from the air currents produced by the rotation of the road wheel and the tire. A stronger suction force will enhance the vacuum's ability to vacuum and remove the excess powder that would otherwise be dispersed throughout the working area.

A third and fourth advantage are provided because the spray nozzle 82 is moveable within the inner housing 48, thus allowing its position to be adjusted relative to the road wheel 94. By positioning the nozzle further away from the road wheel, the powder substance is dispersed over a larger surface area. Alternatively, a more focused deposition is achieved when the nozzle is positioned closer to the road wheel. As such, an operator can adjust the position of the nozzle in order to disperse powder over any surface area that is desired.

In addition, the force of the stream of powder 100 as it strikes the road wheel is decreased when the location of the nozzle is further away. Therefore, the potential for powder becoming removed due to a strong powder force is reduced. Such a result is desirable since increased powder on the road wheel reduces gumming. The ability to place the spray nozzle 82 at a distance away from the road wheel 94 while not compromising the performance of the device is possible because of the stagnant air column that is provided. In known powder dispensing devices, such a stagnant air column is not provided. Therefore, the nozzle must be placed immediately adjacent the road wheel so the turbulent air flow created by the rotating tire and road wheel will not destroy the powder stream. Accordingly, the foregoing advantages associated with the ability to adjust the nozzle position are not obtainable.

A fifth advantage is that the design of the powder dispensing/collection device 10 works equally well regardless of the direction of tire rotation, thereby permitting tire wear testing in either direction of rotation. Bi-directional testing is important in order to simulate left versus right position tire wear. When rotating the road wheel 94 in both the clockwise and counterclockwise direction, particles are discarded in several directions. Providing the vacuum collection chamber 76 with a top and bottom cavity 76*a*, 76*b* ensures that particles thrown from the testing area during either direction of road wheel rotation will be vacuumed regardless of whether the particles are discarded above or below the powder dispersing chamber 50.

Thus, it is apparent that there has been provided, in accordance with the present invention, a powder dispensing/ collection device for indoor tire wear testing which fully satisfies the objects, aims and advantages set forth above. While the invention has been described in conjunction with specific embodiments thereof, it is evident that many alternatives, modifications, and variations will be apparent to those skilled in the art. In light of the foregoing description, accordingly, it is intended to embrace all such alternatives, modifications, and variations as fall within the spirit and broad scope of the appended claims.

We claim:

1. A powder dispensing and collection device for testing of pneumatic tires comprising:

a first housing having an open end suited for facing an abrasive surface of a road wheel;

a second housing at least partially enclosed by the first housing defining a dispensing chamber, the second housing having an open end facing the abrasive surface, at least one interior surface of the first housing and at least one exterior surface of the second housing defining a vacuum collection chamber; and an absorbent media dispensing mechanism located within the dispensing chamber.

2. The dispensing and collection device according to claim 1, wherein the open end of the second housing protrudes out of the first housing so that the open end of the second housing is located closer to the abrasive surface of the road wheel than the open end of the first housing.

3. The dispensing and collection device according to claim 1, wherein the second housing is selectively moveable within the first housing in a direction toward and away from the abrasive surface of the road wheel.

4. The dispensing and collection device according to claim 1, wherein the first housing further comprises first and second adjustable shrouds, each of the first and second shrouds being moveable so that a portion of the first and second shrouds can extend to a variety of positions beyond the open end of the first housing.

5. The dispensing and collection device according to claim 1, wherein the dispensing mechanism is moveable relative to the second housing in a direction toward and away from the abrasive surface of the road wheel.

6. The dispensing and collection device according to claim 5, wherein the dispensing system includes a hose extending through an aperture in the second housing and a nozzle connected to a first end of the hose.

7. The dispensing and collection device according to claim 1, further comprising at least one vacuum duct operatively connected to a rear wall of the first housing, the vacuum duct providing a suction force to the vacuum collection chamber.

8. The dispensing and collection device according to claim 1, wherein the first housing and the second housing are fabricated from galvanized steel.

9. The dispensing and collection device according to claim 1, wherein first and second brush members are attached to opposing edges of the first open portion of the first housing.

10. A testing device for pneumatic tires comprising:
    a road wheel having an abrasive surface;
    a first housing enclosing a vacuum collection chamber, the first housing having an open end adjacent the abrasive surface of the road wheel;
    a second housing at least partially enclosed by the first housing and disposed adjacent the road wheel defining a dispensing chamber, the second housing having an open end facing the abrasive surface of the road wheel; and
    an absorbent media dispensing mechanism located within the dispensing chamber.

11. The testing device according to claim 10, wherein the open end of the second housing protrudes out of the first housing so that the open end of the second housing is located closer to the abrasive surface of the road wheel than the open end of the first housing.

12. The testing device according to claim 10, wherein the second housing is selectively moveable within the first housing in a direction toward and away from the abrasive surface of the road wheel.

13. The testing device according to claim 10, wherein first and second adjustable shrouds are attached to an upper and lower portion of the first housing respectively, each of the first and second shrouds being moveable so that a portion of the first and second shrouds can extend to a variety of positions beyond the open end of the first housing.

14. The testing device according to claim 10, wherein the dispensing mechanism is moveable relative to the second housing in a direction toward and away from the abrasive surface of the road wheel.

15. The testing device according to claim 14, wherein the dispensing system includes a hose extending through an aperture in the second housing and a nozzle connected to a first end of the hose.

16. The testing device according to claim 10, further comprising at least one vacuum duct connected to a rear wall of the first housing, the vacuum duct providing a suction force to the vacuum collection chamber.

17. The testing device according to claim 10, wherein the first housing and the second housing are fabricated from galvanized steel.

18. The testing device according to claim 10, wherein first and second brush members are attached to opposing edges of the first open portion of the first housing.

19. A method for dispersing and collecting an absorbent media during testing of a pneumatic tire comprising the steps of:
    loading a tire against an abrasive surface of a road wheel;
    providing a housing defining a dispensing chamber and a vacuum collection chamber adjacent said road wheel;
    applying the absorbent media to the abrasive surface of the road wheel via a spray nozzle disposed within the dispensing chamber;
    vacuuming excess absorbent media and worn particles into the vacuum collection chamber; and
    transferring the excess absorbent media and worn particles from the vacuum collection chamber to at least one vacuum duct communicating with the vacuum collection chamber.

\* \* \* \* \*